United States Patent [19]

Austin

[11] Patent Number: 4,649,736
[45] Date of Patent: Mar. 17, 1987

[54] MOISTURE MONITORING SYSTEM
[75] Inventor: Robert R. Austin, Pasadena, Calif.
[73] Assignee: ITT Corporation, New York, N.Y.
[21] Appl. No.: 795,026
[22] Filed: Nov. 4, 1985
[51] Int. Cl.[4] .............................................. G01N 27/14
[52] U.S. Cl. ...................................... 73/29; 73/336.5;
338/35
[58] Field of Search ................ 73/29, 335, 336, 336.5;
338/35; 324/65 R, 65 P

[56] References Cited
U.S. PATENT DOCUMENTS

| 2,494,628 | 1/1950 | Oberding | 338/35 |
| 2,629,253 | 2/1953 | Deaton | 73/29 |
| 2,733,607 | 2/1956 | Miller | 73/29 |
| 3,516,282 | 6/1970 | Leach et al. | 73/29 |
| 3,857,284 | 12/1974 | Carron et al. | 73/336.5 |
| 4,041,437 | 8/1977 | Matsuura et al. | 73/29 |
| 4,379,406 | 4/1983 | Bennewitz et al. | 73/336.5 |
| 4,419,988 | 12/1983 | Kitamura et al. | 128/24 R |

FOREIGN PATENT DOCUMENTS

| 2713617 | 10/1978 | Fed. Rep. of Germany | 73/29 |
| 3302447 | 7/1984 | Fed. Rep. of Germany | 73/336.5 |

Primary Examiner—Stephen A. Kreitman
Attorney, Agent, or Firm—T. L. Peterson

[57] ABSTRACT

A moisture monitoring system for continuous flow gas lines, the system having an electrical heater with a salt impregnated sleeve thereabout, with noble metal contacts positioned on the sleeve excited by the AC output of a solid state oscillator and varying in resistance according to water vapor concentration in the gas surrounding the element, with a direct current control signal derived from the AC current to control the direct current to the heating element. A temperature responsive resistor in thermal relation with the heater provides an indication of the moisture content.

19 Claims, 4 Drawing Figures

MOISTURE MONITORING SYSTEM

BACKGROUND OF THE INVENTION

The background of the invention will be discussed in two parts: 1. Field of the Invention This invention relates to moisture monitoring devices, and more particularly to devices for monitoring moisture in a continuous flow high pressure natural gas line.

2. Description of the Prior Art

In high pressure natural gas transmission systems, the natural gas is passed through dehydration apparatus, such as glycol amine moisture absorption treatment units, before delivery to the pipeline. With line pressures in the range of 600 to 800 pounds per square inch, moisture must be reduced to a level below 8 lbs/million cubic feet to avoid condensation at cold locations on the pipeline, or formation of hydrocarton hydrates at such locations.

Dehydration units may operate at high ambient temperature at the production location which can result in low water vapor absorption efficiency during some seasons. Condensation at cold locations on the pipeline can thus occur. It is, therefore, necessary to continuously measure the concentration of water in the natural gas.

Prior art methods of measuring moisture or water content of gases have utilized electrolysis cells and operate on the principle that water can be electrolized by passing direct current through a film of moist phosphorus pentoxide between platinum electrodes. In such instruments a regulated amount of sample gas is flowed through the cell. As water is decomposed to hydrogen and oxygen by electrolysis, a current proportional to the concentration of water vapor in the natural gas at the rate of flow of the natural gas is recorded. In such systems, however, accuracy is highly dependent on the degree of accuracy employed in regulation of the rate of flow of the gas. Furthermore, during periods of excess moisture, cell overload problems are encountered.

As an alternative, solid state moisture sensing elements have been developed for incorporation in electronic circuits, with such elements changing capacitance of the circuit in response to changes in water vapor pressure. However, with such solid state elements, inaccuracies arise as a consequence of contaminants in pipeline gas. Furthermore, with such elements, periodic calibration is required to provide proper measurement of moisture content.

As a means of avoiding regulation of sample flow rates, a number of instrument systems have been developed employing deliquescent salt compounds, such as lithium chloride and lithium bromide. Such salts absorb water vapor at very low pressure to form a conductive solution. The vapor pressure of water in equilibrium with the salt is inversely proportional to the temperature of the sensor in the sample gas chamber. Some instruments of this type utilize conductive electrodes in electrical contact with glass fabric impregnated with one of the salts, with the electrodes connected in an alternating current circuit in series with a resistance heater, supported under, and insulated from, the impregnated fabric. In this system, moisture is absorbed in the salt, forming a conductive film between the electrodes, which, in turn, reduces the resistance in series with the heating element, and correspondingly increases the current through the heating element to increase the heat to therby increase the salt film temperature. As the salt temperature increases, the resistance of the salt film increases due to the increased evaporation of moisture until the resistance of the salt film limits current to the heating element at a level required to sustain the operating temperature. A thermal element records the elevated dew point thus produced. However, in such systems, as a result of the high operating currents normally occurring during high moisture periods, sensor failure is not uncommon with erosion of electrodes and sputtering of hot solutions being encountered.

Exemplary of the prior art is U.S. Pat. No. 2,629,253, issued to Deaton on Feb. 24, 1953 for a "Moisture Content Recorder for Gases Under pressure". In accordance with the teachings of this patent, a sample gas chamber is provided for receciving a preferably purified gas sample, with the chamber being formed in a metallic block having means for creating isothermal conditions within the chamber. A cylindrical member is contained within the chamber and provided with a pair of concentric coils, preferably of palladium wire, wound thereabout in noncontacting relation with each other. The cylindrical element is coated with a deposit of lithium chloride or other suitable salt whose electrical resistivity varies with the moisture content of the surrounding atmosphere. The coils are then electrically connected in a bridge circuit for providing an indication of moisture content at the predetermined isothermal condition.

Although not directed to the extreme environment associated with pipeline moisture content measurements, a prior art system for continuously monitoring ambient relative humidity is shown and described in U.S. Pat. No. 2,733,607, issued Feb. 7, 1956 to Miller for a "Relative Humidity Measuring Instrument". In accordance with the system of this patent, relative humidity sensitive resistance elements are combined with a thermometric, temperature sensitive resistor in a bridge circuit, with unbalances in the bridge being used to drive a motor which in turn positions rheostat wipers to rebalance the bridge, at which point motor operation ceases. The relative humidity sensing element includes a grid of two combs of gold leaf on a substrate, with the teeth of the combs interleaved but not contacting, with a coating of lithium chloride or other suitable hygroscopic material on the substrate.

U.S. Pat. No. 3,516,282, issued June 23, 1970 to Leach et al for a "Dewpoint Detection Apparatus", the system including a fiberglass tube impregnated or coated with a lithium chloride with parallel coils of gold wire wound thereabout. A power supply circuit operating from AC line voltage is used to drive an oscillator, with the coils being connected to the oscillator output having a frequency between 1 kHz and 10 kHz. The alternating current from the oscillator is supplied to the coils from the secondary of a transformer having a first capacitor in series therewith and a second capacitor in parallel therewith to provide parallel and series resonance at various portions of the curing cycle of the system to essentially provide constant power to the coils during the time when excess moisture is being expelled. At equilibrium conditions, the power supply reverts to constant voltage. A second transformer is in series with the output of the first transformer to control an amplifier, which in turn, controls a heater element. A temperature sensitive resistor is contained within the tube for providing an indication of temperature. The use of line voltage and transformers tends to introduce variables into the system, thus reducing accuracy in output measurement.

Another "Humidity Sensor" is shown and described in U.S. Pat. No. 4,041,437, issued Aug. 9, 1977 to Matsuura et al, the sensor being a solid state device with a negative coefficient of resistivity for relative humidity, comprising 99.99 to 10 mole percent of iron oxide and 0.01 to 90 mole percent of at least one member selected from alkali metal oxides, which are lithium oxide, sodium oxide, potassium oxide, potassium oxide and cesium oxide.

An ambient environment humidity measuring system is shown and described in U.S. Pat. No. 4,419,988, issued Dec. 13, 1983 to Kitamura et al, such patent being entitled "Humidity Measuring Method". In this method a current is applied to a thermistor to heat the same to a temperature above open air temperature with the thermistor held in the open air, with the change in resistance value being detected from which the humidity of the air is determined.

A three-terminal semiconductor sensor device for relative humidity measurement circuits is shown and described in U.S. Pat. No. 4,379,406, issued to Bennewitz et al on Apr. 12, 1983, the patent being entitled "Relative Humidity Detector Systems and Method of Increasing the Calibration Period of relative Humidity Detector Systems". The sensor utilizes an essentially pure aluminum oxide layer which has a disordered crystalline structure and a density gradient which varies from a low density at its lower surface to a higher density at its upper surface which together produce the desired linear response to relative humidity.

It is accordingly an object of the present invention to provide a new and improved moisture monitoring apparatus for use in high pressure gas pipeline.

It is another object of the present invention to provide a new and improved moisture monitoring apparatus for use in a high pressure gas pipeline for providing an indication of moisture independent of flow rate of the gas.

It is still another object of the present invention to provide a new and improved moisture monitoring apparatus having solid state control and measurement circuitry with direct current control of the heater thereof.

It is a further object of the present invention to provide a new and improved moisture monitoring apparatus which is highly reliable and accurate.

SUMMARY OF THE INVENTION

The foregoing and other objects are accomplished by providing a moisture sensor including a sleeve of fiber glass fabric impregnated with LiBr salt with spaced noble metal electrodes in electrical contact therewith, the resistance between the sensor electrodes varying with the moisture responsive resistivity of the salt film therebetween. A solid state oscillator circuit biased with a regulated DC supply provides a low current alternating current to the electrodes. A signal is derived from the output for controlling a gate semiconductor in series relation with a heater element in thermal relation with the sleeve, the power to the heater being supplied from the regulated DC source. A resistance thermal detector mounted within the sleeve is in thermal relation with the heater and is connected in circuit relation with a high accuracy solid state instrumentation amplifier to provide an output indicative of moisture content.

Other objects, features and advantages of the invention will become apparent from a reading of the specification, when taken in conjunction with the drawings, in which like reference numerals refer to like elements in the several views.

DESCRIPTION OF THE PREFERRED EMBODIMENT

Figure 1:
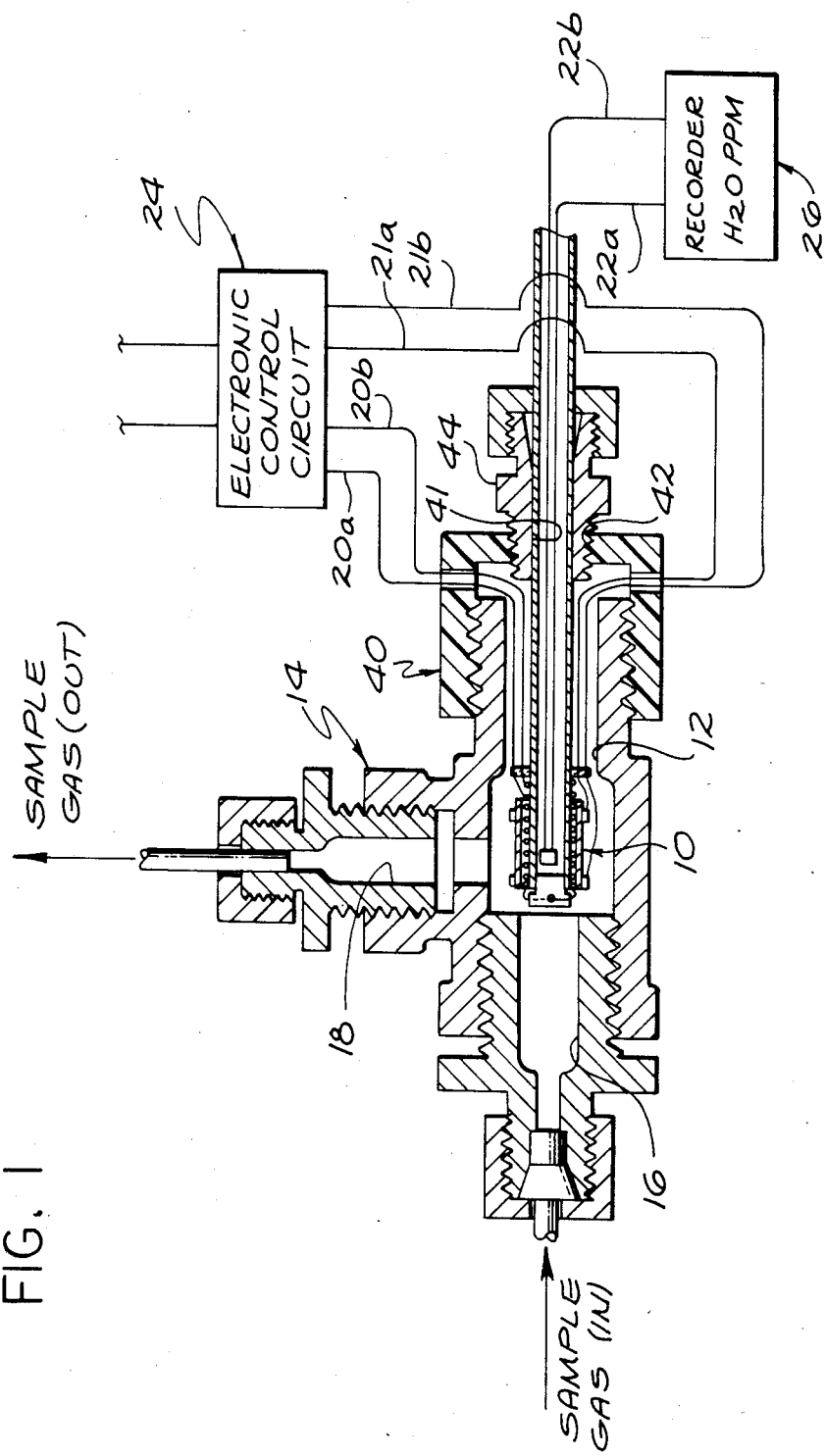
FIG. 1 is a cross-sectional view of a moisture monitoring apparatus in accordance with the present invention assembled for receiving gas flow from a pipeline.

Referring now to the drawings, and particularly to FIG. 1, there is shown a moisture monitor assembly, including the sensor assembly, generally designated 10, mounted within a chamber 12 of a housing, generally designated 14, the housing being in the form of a fitting attachable to receive gas from a pipeline at line pressures, typically about 800 pounds per square inch.

The housing 14 is in the form of a pipe fitting with an inlet port 16 and an outlet port 18 in fluid flow communication with the chamber 12. Secured within the chamber 12 is the sensor assembly 10 which is provided with three pairs of electrical leads 20-22 extending therefrom to the exterior of the housing 12, lead pairs 20a and 20b, and 21a and 21b being coupled to an electronic control circuit 24, with lead pair 22a and 22b being coupled to a moisture content recorder 26.

Figure 2:
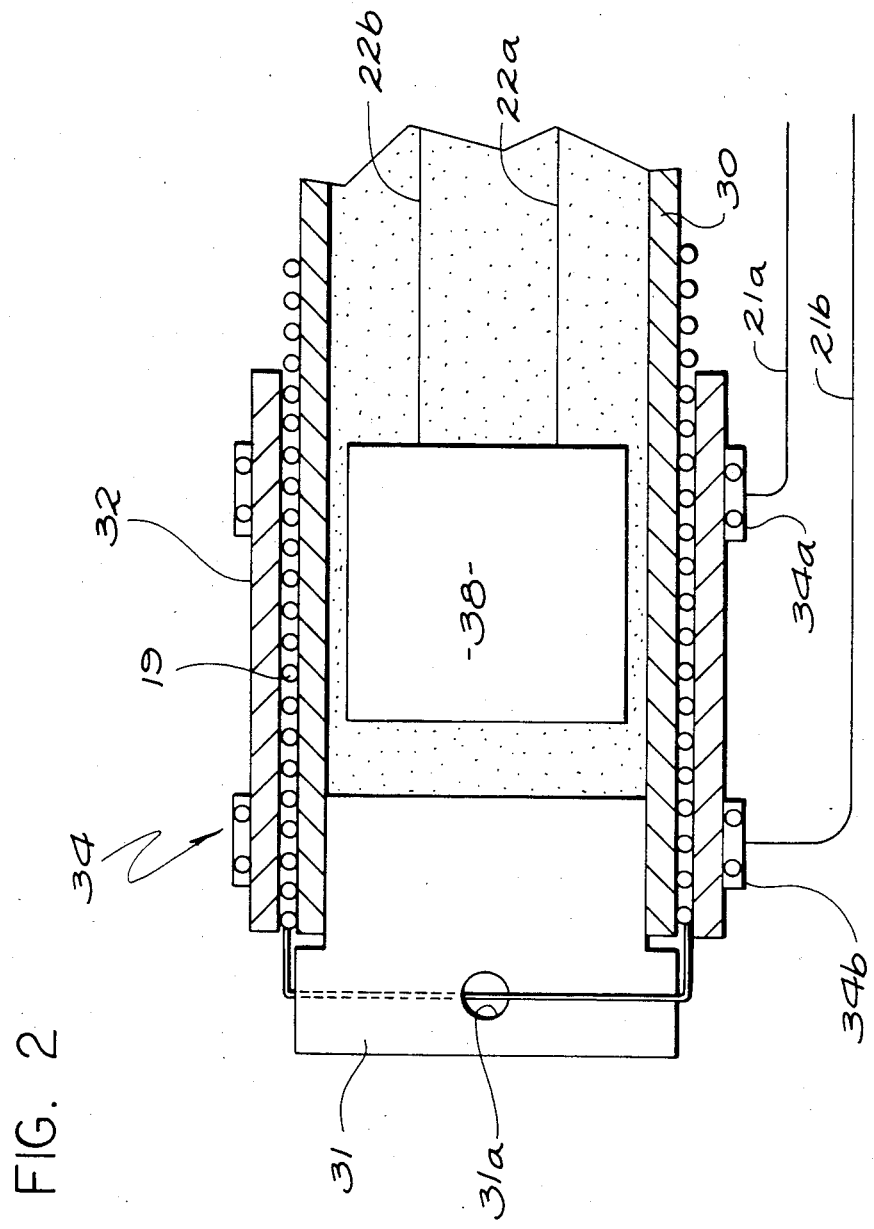
FIG. 2 is a diagramatic cross-sectional view of sensor assembly of the moisture monitoring apparatus of FIG. 1.

Referring now to FIGS. 1 and 2, the construction of the sensor assembly 10 will be described, and includes a heating means comprised of tubular inner sleeve 30 of highly thermally conductive metal, such as Monel or stainless steel, having wound thereabout a bifilar heating element or coil of wire 19, such as enamel insulated nichrome wire, with the wires connected to leads 20a and 20b to the control circuit 24. One end of the sleeve 30 is closed and sealed with a high temperature insulating plug member 31 which is provided with a throughhole 31a for the passage therethrough of a portion of the winding of wire 19. The plug 31 may, for example, be formed of a bakelite material. In intimate thermal relation with the heating means, but electrically insulated therefrom, is a tubular sleeve or former 32 of fiber glass encircling the heating wire 19, with the former 32 being coated, or preferably impregnated, with a salt material such as lithium bromide, or any other salt which has the characteristic of moisture absorption while providing an electrically conductive path with a resistance varying in inverse relation to the moisture content of the gases surrounding the salt layer.

An alternating current sensor 34 is formed of annular electrodes 34a and 34b which are positioned on former 32 in electrically conductive relation with the salt layer thereof, and in spaced relation to each other, the annular electrodes 34a and 34b being formed of a noble metal, such as platinum, and epoxy. The leads 21a and 21b connect to the electrodes 34a and 34b for electrical connection to the control circuit 24. Affixed within the inner sleeve 30, and positioned generally centrally relative thereto, is a resistance thermal detector 38 which is electrically connected to leads 22 to the moisture content recorder 26. The interior of the sleeve 30 surrounding the detector 38 is suitably filled with an inert thermally conductive material such as aluminum oxide.

As shown in FIG. 2, the inner sleeve 30 is longer than the former 32, and is secured within a central axially extending aperture 41 of a junction block 40, which may be constructed of a high temperature electrically and thermally insulating material such as a plastic phenolic material. At the opposite end, the junction block 40 is provided with a necked-down portion 42 to which is secured a stainless steel conduit 44. Suitable openings are provided in the junction block 40 for passage therethrough of the leads 20–22, which then pass through the conduit 44 for electrical connection to the external control circuit 24 and recorder 26.

Figure 3:
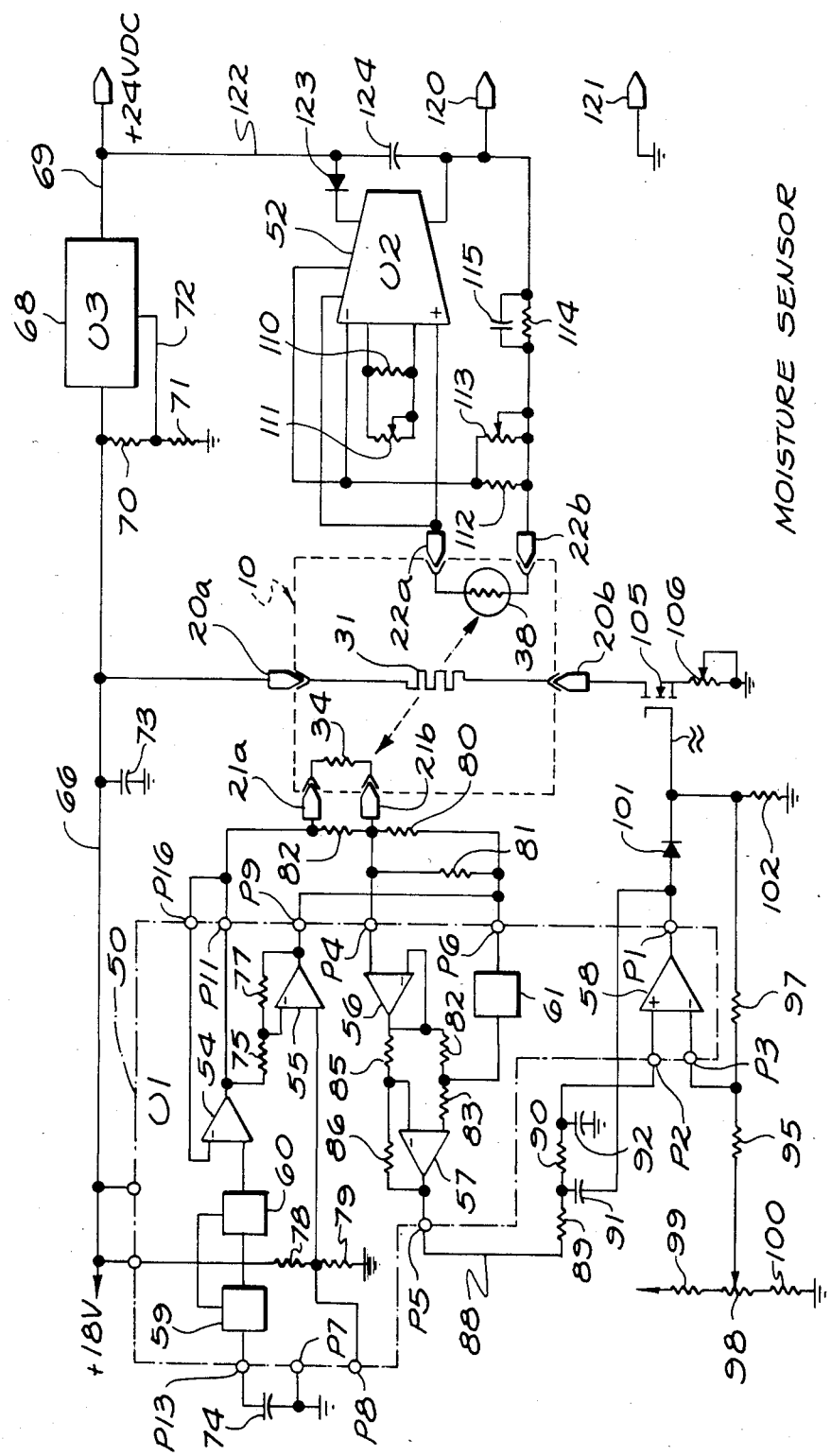
FIG. 3 is a schematic circuit of the moisture monitoring apparatus according to the invention.

Referring now to FIG. 3, the details pertaining to the electronic circuitry will be described. In brief, the circuitry includes three main functional portions, these being a highly regulated oscillator section, a heater control section, and a detection and recording section. In the circuitry, two primary integrated circuits are employed, these being designated U1 and U2 in the drawing, with U1 (shown enclosed in dotted lines and bearing the reference numeral 50) being a signal conditioning circuit of Signetics designation SE5520, and U2 (shown in solid lines and bearing reference numeral 52) being a high accuracy instrumentation amplifier of Burr-Brown Corporation designation XTR100. The outer perimeter of the signal conditioning circuit 50 is provided with small circles, with numerals adjacent thereto, these numerals referring to pin connections of the integrated circuit 50. Similarly, the perimeter of amplifier 52 has numerals adjacent thereto, these numerals referring to pin connections therefor. A description of the technical parameters may be had by reference to published information of the manufacturers of such circuits. Electrical connections to such devices will be made with reference to the pin numbers depicted, with such pin numbers being preceded by the letter "P" to avoid confusion with other reference numerals.

The signal conditioning circuit 50 includes a plurality of on board operational amplifiers 54–58, with a triangle wave oscillator 59, a sine converter 60 and a synchronism demodulator 61. The circuit 50 is a fourteen pin circuit with resistors and capacitors of appropriate value therein, as well as the interconnections therebetween. A fixed reference bias voltage to the circuit 50 is provided via pin P12 over lead 66 from a highly regulated voltage source supplied through voltage regulator 68, which is an integrated circuit bearing manufacturer's designation LM317. The input is an unregulated source of 24 volts D.C. applied to regulator 68 over input lead 69. Bias is provided for the regulator 68 by means of resistors 70 and 71 connected in series between output lead 66 and ground, with resistor 70 having a value of 243 ohms and resistor 71 having a value of 3.24k ohms, these two resistors acting as a voltage divider, with the interconnection thereof providing a feedback signal via lead 72 to the regulator 68. A smoothing capacitor 73 is connected between lead 66 and ground.

As will be described hereinafter, the output of the regulated voltage supply on lead 66, in addition to providing power for the signal conditioning circuit 50, also supplies this highly regulated direct current power to the heater element 19, shown enclosed within a dotted line block, designated 10, this block schematically representing the sensor assembly 10 previously described. Also schematically designated within the assembly 10 are the alternating current sensor 34 and the resistance thermal detector 38. The electrical connections for such devices bear the same reference numerals for the leads heretofore described in connection with FIGS. 1 and 2.

Referring again to the signal conditioning circuit 50, triangle wave oscillator 59 has the input thereof connected to a capacitor 74 at circuit pin P13, the other end of the capacitor 74 being coupled to ground. Capacitor 74 is 0.1 microfarads in value and establishes the oscillating frequency of the oscillator 59, the output of which is fed to the sine convertor 60, this output then being provided to the non-inverting input of opamp 54, the output of which is cross-coupled to the inverting input externally of the circuit 50 by interconnection of pins P10 and P11. This output is also provided to the inverting input of the opamp 55 through series resistor 75 (10k ohms), with the output and inverting input of opamp 55 being interconnected via resistor 77 (10k ohms). The non-inverting input of opamp 55 receives a reference bias from the midpoint of a voltage divider including resistors 78 and 79 connected between the bias voltage appaearing at pin P12 and ground, each of these resistors 78 and 79 having a value of 10k ohms.

The output of circuit 50 appearing at pins P10 and P11 provides a "push-pull" sine wave excitation frequency within the audio range, which is then applied to the alternating current sensor 34. For this purpose, pin P10 is connected to lead 21a of the sensor 34, and pin P9, which is the output of opamp 55 is connected to the other lead 21b through parallel resistors 80 (10k ohms) and 81 (47k ohms). A resistor 82 (10k ohms) is connected in parallel with sensor 34. The current provided to sensor 34 is then monitored across resistor 81, one end of which is coupled to the non-inverting input of opamp 56, with the other end of resistor 81 providing an input to a synchronous demodulator 61, the output of which is coupled to the midpoint of series coupled resistors 82 and 83 (5k ohms each). One end of the series connected resistors 82, 83 is connected to the output of opamp 56 which is cross-coupled to its inverting input. The other end of resistor 83 is coupled to the non-inverting input of opamp 57, the inverting input of which is connected through resistor 85 (10k ohms) to the output of opamp 56 and also to its own output via resistor 86 (10k ohms), this output appearing on pin P5.

From pin P5 an external lead 88 provides an input to an onboard amplifier 58 via pin P2 with a filter circuit connected therebetween, the filter circuit including series resistors 89 (4.7k ohms) and 90 (24k ohms), with a first capacitor 91 (0.1 microfarad) connected from the interconnection of the two resistors to the output of amplifier 58, and a second capacitor 92 (0.22 microfarad) connected between pin P2 (the non-inverting input of amplifier 58) and ground.

The inverting input of amplifier 58 appears at pin P3, which is coupled to a voltage divider at the midpoint of resistors 95 (121k ohms) and 97 (1.2 megohms). The other end of resistor 95 is coupled to the movable tap of a rheostat 98 (10k ohms), which is connected in series with resistors 99 (10k ohms) and 100 (10k ohms) between the positive source of regulated voltage (lead) and ground. The output of amplifier 58 appears at pin P1, where it is connected to a diode 101, the other end of which is coupled to resistor 97, and to another resistor 102 (10k ohms) which is connected to ground.

The heater control section includes the heater 19 coupled to the regulated voltage source via connector lead 20a to lead 66, with the heater 19 in series with a switching transistor, which has the base thereof coupled for control by the diode 101, and the emitter coupled through a gain adjust rheostat 106 to ground. Changes in temperature are sensed by the resistance thermal detector 38 which has a variable resistance with a nominal central point resistance of approximately 100 ohms at 0° C.

Detector 38 provides the input to the detection and recording section which includes the integrated circuit 52, which is a high accuracy instrumentation amplifier, and provides signal conditioning of the input signal from the detector 38. Pins P5 and P6 have connected thereacross a "zero adjust" circuit, which includes two resistors in parallel, one resistor 110 being a fixed resistor of 57.6 ohms, and the other resistor 111 being variable with a resistance of 5k ohms. Non-inverting input at pin P4 is cross-coupled to pin P11 and also connected directly to one end of detector 38 through connecting leads 22, while the other of detector 38 is connected through lead 22b through a "span adjust" resistance bridge to both pins P10 and P3 (the inverting input) of amplifier 52. The span adjust bridge includes fixed resistor 112 (124 ohms) in parallel with variable resistor 113 (5k ohms). Detector lead 22b is also connected through a parallel RC circuit (resistor 114 at 2.49k ohms, and capacitor 115 at 0.01 microfarads) to output terminal 120, the other output terminal being ground and designated 121. Power to the amplifier 52 is provided from the unregulated source appearing on lead 69 at 24 volts d.c. over lead 122 through diode 123 to pin P8 thereof, with a capacitor in the path between lead 122 and output terminal 120, which is also connected to pin P7 of amplifier 52.

Figure 4:
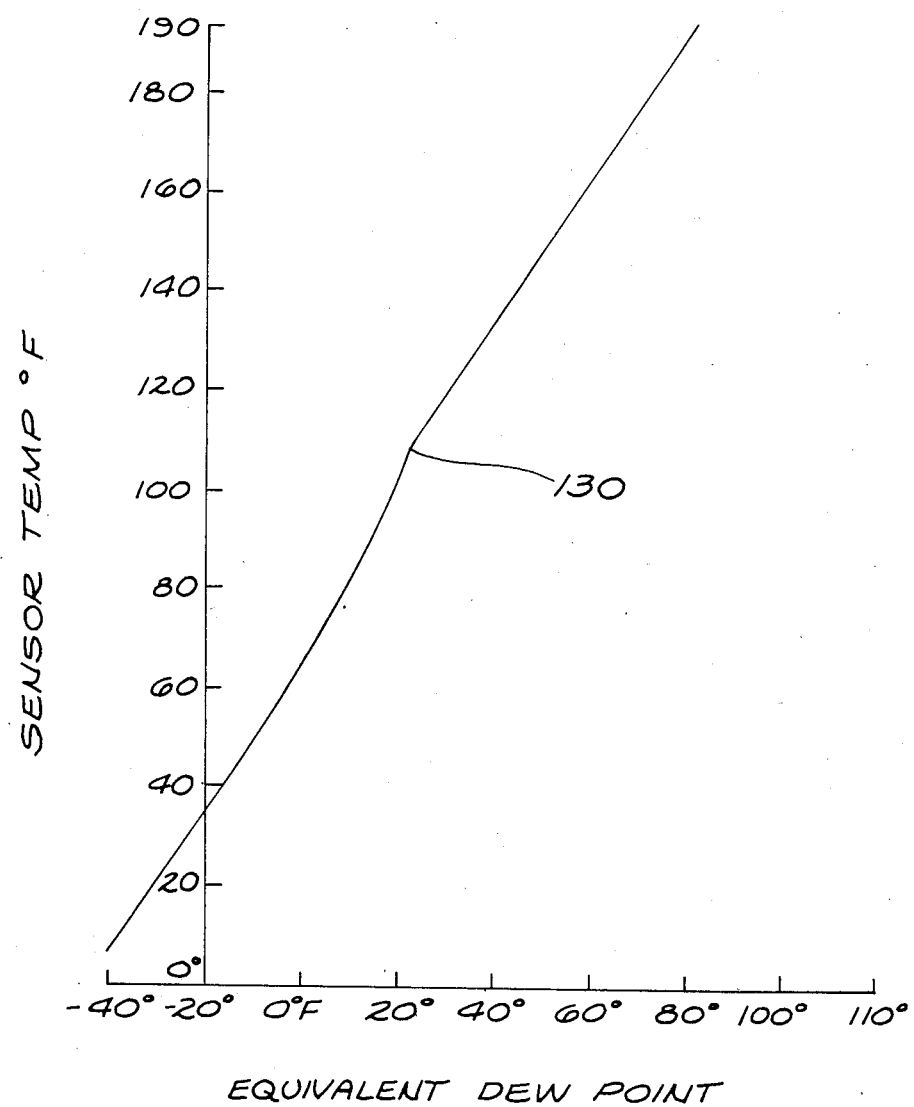
FIG. 4 is a graphical depiction of the readout of the moisture monitoring circuit of FIG. 2.

The output appearing at terminals 120 and 121 are connected to suitable recording and/or monitoring devices 26 (See FIG. 1) which provide an indication of dew point within the gas measurement assembly chamber 12 of the sensor 10. The curve FIG. 4 is a plot of the data for the temperature of the sensor element with lithium bromide detector compound in equilibrium with vapor pressure of water at the indicated dewpoint. The sensor temperature control circuit is designed to maintain the temperature of the sensor element corresponding to the sensor temperature versus equivalent dewpoint curve temperature.

In operation, the system is based on the Lithium Bromide absorption of moisture and the maintenance of the sensor 34 at the temperature representing equilibrium of vapor pressure in the gas within the chamber 12 to the vapor pressure of water in the salt film appearing between the electrodes which form the sensor 34. With noble metal electrodes 34, and particularly platinum, mounted in contact with fiber glass fabric 32 impregnated with LiBr salt, the resistance of the salt film element of a high frequency AC circuit will vary reproducibly inversely proportional to water vapor concentration in the gas surrounding the salt film element.

This high frequency AC power is derived by means of the signal conditioning circuit 50 which provides a very stable push pull alternating current source across the electrodes of sensor 34, this alternating current originating with the triangle wave generator 59, which is converted to a sine wave via converter 60, with amplifiers 54 and 55 then providing the alternating current to the sensor. With the circuit as shown, the current flowing through the sensor 34 can be limited to a very low range of up to approximately 200 microamps, which avoids the destructive tendencies normally associated with higher currents in such devices, such as sputtering or rapid deterioration of the noble metal electrodes.

This alternating current is then sensed at pins P4 and P6 of circuit 50, where the tandem action of amplifiers 56 and 57 along with synch demodulator 61 produces a pulsating direct current signal at pin P5 on lead 88, this pulsating signal providing a signal indicative of the current flowing through the sensor electrodes 34, which in turn is indicative of the water vapor within the salt film. As the water vapor increases, the resistance appearing between the sensor electrodes 34 decreases, that is there is inverse proportionality.

This pulsating d.c. signal on lead 88 is then filtered and smoothed to provide a direct current control signal to the gain amplifier 58, which in turn controls the amount of current through the transistor 105 above a certain threshold level. As the voltage appearing at the base of transistor 105 increases, the amount of current passing through transistor 105 increases, thereby increasing the current through the heater 19, which has a resistance of between 250 and 400 ohms. For this circuit, variable resistor 98 serves as a cutoff adjustment, while variable resistor 10 serves as a gain adjustment.

This direct current control signal can be derived from the ac flow in the sensing circuit and applied as an input to an operational amplifier circuit 58 which is connected to supply current through the heater 19, which is insulated from the sensing circuit and mounted to heat the tubular former 30 on which the sensing salt bridge and electrodes 34 are assembled.

Changes in heater 19 current controls the resistance of the resistance thermal detector 38, which in turn controls the output appearing at output terminals 120 and 121. With the detector 38 mounted and encased internally in the tubular support 30 for the sensing electrodes 34, the salt film will be heated by the resistance heater 19 as moisture is absorbed in the LiBr sensor film of the fabric 32. As temperature of the sensing electrodes 34 increases, resistance of the salt film is increased by loss of moisture, thus decreasing the input signal to amplifier 58 until only sufficient current flows in the heater 19 to maintain temperature of the salt film so that equilibrium between water vapor pressure in gas phase is equal to vapor pressure of absorbed water in the salt film. The resistance of the detector 38 within the support tube 30 is thus proportional to the temperature of the sensing electrodes 34 of the assembly.

In accordance with the present invention there is provided a moisture monitoring system having a detector which is independent of gas sample flow rate over a substantial range of flow. It is only necessary to regulate pressure within the sample chamber 12, and to record the signal derived from the detector element 38 in order to record the moisture level in pipeline gas. The instrumentation amplifier 52 can be adjusted to convert the detector 38 resistance signal to a 4-20 milliamp signal and to a standard recorder which can read out as ppm or pounds of water vapor per million cubic feet of natural gas.

While there has been shown and described a preferred embodiment, it is to be understood that various other adaptations and modifications may be made within the spirit and scope of the invention.

I claim:

1. In an apparatus for measuring the moisture content of a sample gas within a chamber, the combination comprising:
   a source of regulated direct current;
   heating means within the chamber coupled to said source;
   control means in series circuit relation with said heating means;
   a salt impregnated fabric in thermal contact with said heating means within said chamber;
   noble metal sensing electrode means in electrically conductive relation with said fabric;
   circuit means coupled to said source for supplying an alternating current to said electrode means;
   means for deriving a control signal from said circuit means for controlling said control means and varying the application of current to said heating means;
   thermally responsive means in thermal relation with said heating means; and
   output means electrically coupled to said thermally responsive means for providing a signal proportional to the moisture content of the sample gas within said chamber.

2. The apparatus of claim 1 wherein said heating means are insulated from said electrode means.

3. The apparatus according to claim 1 wherein said means for deriving a control signal includes means coupled in circuit relation with said sensing electrode means.

4. The apparatus according to claim 1 wherein said apparatus includes a tubular support member and said heating means is a coil wound about said support member with said fabric wrapped about said coil and said sensing electrode means about said fabric.

5. The apparatus according to claim 4 wherein said thermally responsive means are within said support member.

6. The apparatus according to claim 5 wherein said salt impregnated fabric is a fiber glass fabric impregnated with a lithium bromide salt.

7. The apparatus according to claim 6 wherein said noble metal sensing electrode means are platinum electrodes.

8. The apparatus according to claim 1 wherein said circuit means supplies an alternating current of 200 microamps or less.

9. The apparatus according to claim 8 wherein said circuit means supplies an alternating current having a frequency in the audio range.

10. The apparatus according to claim 9 wherein said control means is a current control semiconductor device.

11. In an apparatus for measuring the moisture content of a sample gas within a chamber, the combination comprising:
    a sensor assembly within the chamber including
    a tubular support member,
    a heating coil wound about said support member,
    a salt impregnated fabric about said heating coil in intimate thermal relation therewith,
    noble metal sensor means about said fabric, said sensor means being insulated from said heating coil, and
    thermally responsive means within said tubular support member in thermal relation with said heating means, and
    electrical means including
    a source of regulated direct current,
    means coupling said heating coil to said source,
    control means in series circuit relation with said heating coil,
    circuit means coupled to said source for supplying an alternating current to said sensor means,
    means for deriving a control signal from said circuit means for varying said control means for controlling the application of current to said heating coil, and
    output means electrically coupled to said thermally responsive means for providing a signal proportional to the moisture content of the sample gas within said chamber.

12. The apparatus according to claim 11 wherein said salt impregnated fabric is impregnated with a lithium bromide salt.

13. The apparatus according to claim 12 wherein said noble metal sensing electrode means are platinum electrodes.

14. In a sensor assembly for placing within a chamber for measuring the moisture content of a sample gas within the chamber, the combination comprising:
    a tubular support member;
    a heating coil wound about said support member;
    a salt impregnated fabric about said heating coil in intimate thermal relation therewith;
    noble metal sensor means on said fabric in electrically conductive relation therewith, but insulated from said heating coil; and
    thermally responsive means within said tubular support member in thermal relation with said heating means.

15. The sensor assembly according to claim 14 wherein said noble metal sensor means are platinum electrodes.

16. The sensor assembly according to claim 15 wherein said salt impregnated fabric is a fiber glass fabric impregnated with lithium bromide salt.

17. The sensor assembly according to claim 16 wherein said thermally responsive means is a temperature sensitive resistance device encapsulated within said support member.

18. The apparatus according to claim 17 wherein said support member is thermally conductive.

19. The apparatus according to claim 18 wherein said support member is formed of one of monel and stainless steel and said heating coil is electrically insulated therefrom.

* * * * *